United States Patent [19]

Gilpin

[11] Patent Number: 4,463,010

[45] Date of Patent: Jul. 31, 1984

[54] 1-AZA-[3.2.0]-BICYCLOHEPTANE-2-CARBOXYLIC ACID, ESTER OR SALT THEREOF

[75] Inventor: Martin L. Gilpin, Reigate, England

[73] Assignee: Beecham Group p.l.c., England

[21] Appl. No.: 377,671

[22] Filed: May 12, 1982

[30] Foreign Application Priority Data

May 14, 1981 [GB] United Kingdom ................ 8114847
Jan. 21, 1982 [GB] United Kingdom ................ 8201642

[51] Int. Cl.$^3$ ................ A61K 31/425; A61K 31/42; C07D 499/42; C07D 499/46; C07D 263/00
[52] U.S. Cl. ................ 424/270; 260/239 R; 260/239.1; 260/245.2 R; 260/245.3; 424/211; 424/272; 548/180
[58] Field of Search ......... 260/239 R, 239.1, 245.2 R, 260/245.3; 548/180; 424/272, 271, 270

[56] References Cited

U.S. PATENT DOCUMENTS

| 4,076,826 | 2/1977 | Christensen et al. ........ 260/245.3 X |
| 4,078,067 | 3/1976 | Christensen et al. ........ 260/245.3 X |
| 4,088,656 | 5/1978 | Howarth et al. ................. 260/245.3 |
| 4,138,403 | 2/1979 | Howarth et al. ................. 260/245.3 |
| 4,194,047 | 3/1980 | Christensen et al. .... 260/245.2 R X |
| 4,206,219 | 6/1980 | Christensen et al. ...... 260/239 A X |
| 4,210,662 | 7/1980 | Eglington et al. ........ 260/245.2 R X |

Primary Examiner—Natalie Trousof
Assistant Examiner—Vera C. Clarke
Attorney, Agent, or Firm—Jacobs & Jacobs

[57] ABSTRACT

A 1-aza[3.2.0]bicycloheptan-2-carboxylic acid or salt or ester thereof having a substituent at position 7 of the formula:

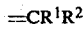

$=CR^1R^2$ wherein $R^1$ and $R^2$ are independently hydrogen, halogen or an organic group.

26 Claims, No Drawings

1-AZA-[3.2.0]-BICYCLOHEPTANE-2-CARBOXYLIC ACID, ESTER OR SALT THEREOF

This invention relates to a class of novel chemical compounds and in particular to a class of modified $\beta$-lactam compounds.

Bicyclic $\beta$-lactam compounds are known to have antibacterial and/or $\beta$-lactamase inhibitory activity. A class of modified $\beta$-lactam derivatives have now been found which are useful as intermediates and also possess some synergistic activity in combination with other $\beta$-lactam compounds. Bicyclic $\beta$-lactam compounds having a 5-membered ring fused to the 4-membered $\beta$-lactam ring are termed 1-aza-7-oxo[3.2.0]bicycloheptane carboxylic acids.

The present invention provides a 1-aza[3.2.0]bicycloheptan-2-carboxylic acid or a salt or ester thereof having a substituent at position 7 of the formula

$=CR^1R^2$ wherein $R^1$ and $R^2$ are independently hydrogen, halogen, or an organic group.

As the compounds of this invention are of use primarily as intermediates, a carboxylic ester of the compounds need not be pharmaceutically acceptable. When the compounds are to be employed as pharmaceuticals, then a pharmaceutically acceptable salt or ester would be chosen.

Suitable esters of the compounds of the invention include those cleavable by biological methods such as enzymatic hydrolysis, in-vivo hydrolysis, and those cleavable by chemical methods such as hydrogenolysis, hydrolysis, electrolysis or photolysis.

Suitably the carboxylic acid is esterified by a group of the sub-formula (a), (b), (c), (d), (e) or (f):

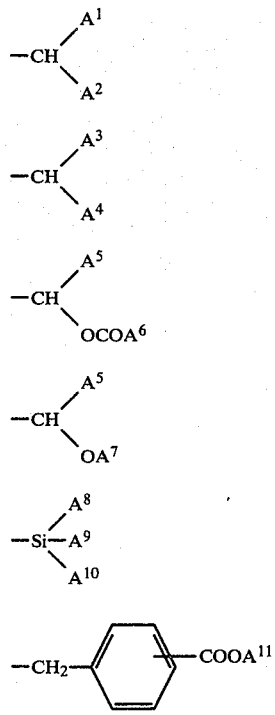

wherein $A^1$ is a hydrogen atom, $C_{1-6}$ alkanoyl or an $C_{1-5}$ alkyl group optionally substituted by $C_{1-7}$ alkoxy or $C_{1-7}$ carboxylic acyloxy, or an alkenyl or alkynyl group of up to 5 carbon atoms; $A^2$ is a hydrogen atom or a methyl group; $A^3$ is a phenyl group or a phenyl group substituted by a fluorine, chlorine or bromine atom or a nitro, $C_{1-3}$ alkyl or $C_{1-3}$ alkoxy group; $A^4$ is a hydrogen atom or a phenyl group or phenyl group substituted by a fluorine, chlorine or bromine atom or a nitro, $C_{1-3}$ alkyl or $C_{1-3}$ alkoxy group; $A^5$ is a hydrogen atom or a methyl group; $A^6$ is a $C_{1-4}$ alkyl, phenyl or $C_{1-4}$ alkoxy group or $A^5$ is joined to $A^6$ to form a phthalidyl, dimethylphthalidyl or dimethoxyphthalidyl group; $A^7$ is a $C_{1-4}$ alkyl, phenyl, chlorophenyl or nitrophenyl group; $A^8$ is a $C_{1-4}$ alkyl or phenyl group; $A^9$ is a $C_{1-4}$ alkyl or phenyl group; $A^{10}$ is $C_{1-4}$ alkyl; and $A^{11}$ is $C_{1-4}$ alkyl: or $CHA^1A^2$ is a phenacyl or bromophenacyl group.

Favourably $A^1$ is a hydrogen atom or a methyl, ethyl, vinyl or ethenyl group. Favourably $A^2$ is a hydrogen atom. Favourably $A^3$ is a phenyl, p-bromophenyl, p-methoxyphenyl or p-nitrophenyl group. Favourably $A^4$ is a hydrogen atom. Favourably $A^6$ is a methyl, t-butyl or ethoxy group or is joined to $A^5$. Favourably $A^7$ is a methyl group.

Preferred groups of the sub-formula (a) include the methyl, ethyl and acetonyl groups.

Preferred groups of the sub-formula (b) include the benzyl and p-nitrobenzyl groups.

Preferred groups of the sub-formula (c) include the acetoxymethyl, pivaloyloxymethyl, α-ethoxycarbonyloxymethyl and phthalidyl groups.

A preferred group of the sub-formula (d) is the methoxymethyl group.

Preferred groups of the sub-formula (e) include the trimethylsilyl, tert-butyldimethylsilyl and tert-butyldiphenylsilyl groups.

A preferred group of the sub-formula (f) is p-methoxycarbonylbenzyl.

Particularly preferred esterifying groups are the p-nitrobenzyl and phthalidyl groups.

Pharmaceutically acceptable in-vivo hydrolysable esters are those esters which hydrolyse in the human body to produce the parent acid or its salt. Such esters may be identified by administration to a test animal such as a rat or mouse by intravenous administration and thereafter examining the test animal's body fluids for the presence of the compound of the invention or its salt.

Suitable ester groups of this type include those of part formulae (g), (h) and (i):

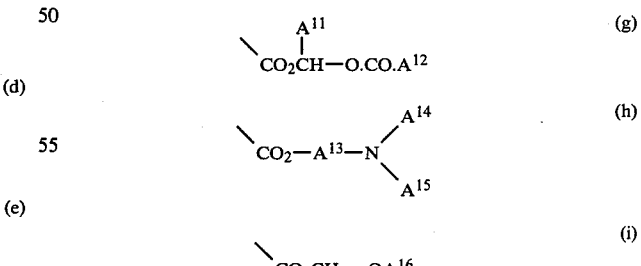

wherein $A^{11}$ is hydrogen, methyl, or phenyl, $A^{12}$ is $C_{1-6}$ alkyl, $C_{1-6}$ alkoxy or phenyl; or $A^{11}$ and $A^{12}$ together form a 1,2-phenylene group optionally substituted by one or two methoxy groups; $A^{13}$ represents $C_{1-6}$ alkylene optionally substituted with a methyl or ethyl group; $A^{14}$ and $A^{15}$ independently represent $C_{1-6}$ alkyl; $A^{16}$ represents $C_{1-6}$ alkyl. Examples of suitable in vivo hydrolysable ester groups include acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, diethylaminoethyl, phthalidyl and dimethoxyphthalidyl groups.

Suitable pharmaceutically acceptable salts of the carboxylic acid group of the compound of the invention include metal salts, eg aluminium, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydrobietylamine, N,N'-bisdehydrobietyl-amine, ethylenediamine, or bases of the pyridine type such as pyridine, collidine or quinoline, or other amines which have been used to form salts with known penicillins.

The groups $R^1$ and $R^2$ are the same or different and each represents hydrogen, halogen or an organic group. Preferably one of $R^1$ and $R^2$ represents hydrogen. Suitable halogen atoms are bromine and chlorine. When $R^1$ or $R^2$ is an organic group, it is suitably a $C_{1-10}$ hydrocarbon group, for example a $C_{1-6}$ alkyl group, optionally substituted with a functional substituent, such as hydroxy, carboxy or $C_{1-6}$ alkoxycarbonyl.

Preferably $R^1$ or $R^2$ is an electron withdrawing group such as cyano, $C_{1-6}$ alkylcarbonyl, or esterified carboxyl, for example alkoxycarbonyl, aryloxycarbonyl or aralkoxy carbonyl, wherein the alkyl portions have from 1 to 6 carbon atoms. The aryl portions include phenyl and phenyl substituted with, for example chloro, bromo, nitro or $C_{1-6}$ alkyl.

When $R^1$ is hydrogen, preferably $R^2$ is methoxycarbonyl, or ethoxycarbonyl.

Suitable 1-aza[3.2.0]bicycloheptanes of this invention include the following structures (I), (II) and (III): or salts or esters thereof:

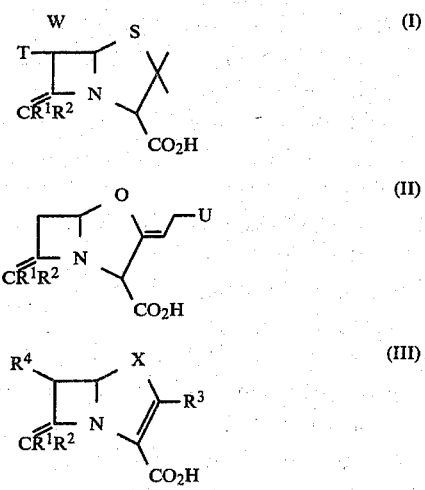

wherein T represents hydrogen, amino or acylamino; W represents hydrogen, arylthio, $C_{1-6}$ alkylthio or methoxy; U represents hydroxyl, substituted hydroxyl, thiol, substituted thiol, amino, mono- or di-hydrocarbyl-substituted amino, or mono- or di-acylamino; $R^3$ represents hydrogen or an organic group bonded via sulphur or carbon; $R^4$ represents hydrogen or an organic group bonded via a carbon atom; X represents —S— or —CH—; and $R^1$ and $R^2$ are as defined above.

Suitable groups W include hydrogen, phenylthio, p-methylphenylthio, methylthio and methoxy.

Suitably the group T represents hydrogen or amino or is an organic acylamino group such as is found in antibacterially effective penicillins. Thus suitable groups T include those of sub-formulae (i), (ii), (iii) and (iv):

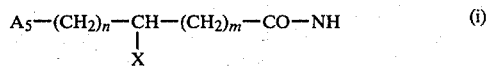

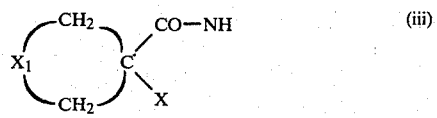

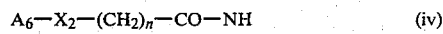

wherein n is 0, 1 or 2; m is 0, 1 or 2; $A_5$ is an alkyl group of 1 to 6 carbon atoms, a cycloalkyl group of 3 to 6 carbon atoms, cyclohexenyl, cyclohexadienyl, phenyl hydroxyphenyl, thienyl or pyridyl group; X is a hydrogen, bromine or chlorine atom, a carboxy group, carboxylate salt, carboxylate ester, sulpho, hydroxy, acyloxy, amino, heterocyclylamino, ureido, guanidino or acylureido group; $A_6$ is an aromatic group such as a phenyl, 2,5-dimethoxyphenyl, 2-alkoxy-1-naphthyl, 3-arylisoxazolyl, isothiazolyl or 3-aryl-5-methylisoxazolyl group; $X_1$ is a $CH_2OCH_2$, $CH_2SCH_2$ or $(CH_2)_n$ group; and $X_2$ is an oxygen or sulphur atom. For example, phenylacetamido, p-hydroxyphenylacetamido, o-hydroxyphenylacetamido, m-hydroxyphenylacetamido, α-chlorophenylacetamido, α-bromophenylacetamido, α-carboxyphenylacetamido and esters thereof such as the methylphenyl, indanyl and phenyl esters, α-azidophenylacetamido, α-aminophenylacetamido, α-hydroxyphenylacetamido, α-ureidophenylacetamido, α-guanidinophenylacetamido, α-(acetylureido)phenylacetamido, α-acetoxyphenylacetamido, α-tetrazolylphenylacetamido, acetamido, chloroacetamido, bromoacetamido, propionamido, pyridylacetamido, 2-thienylacetamido, 3-thienylacetamido, 2-thienylpropionamido, 3-thienylpropionamido, α-chloro(p-hydroxyphenyl)acetamido, α-bromo(p-hydroxyphenyl)acetamido, α-carboxy(p-hydroxyphenyl)acetamido and esters thereof such as the methylphenyl, indanyl and phenyl esters α-amino(p-hydroxyphenyl)acetamido, α-hydroxy(p-hydroxyphenyl)acetamido, α-acetoxy(p-hydroxyphenyl)acetamido, α-ureido(p-hydroxyphenyl)acetamido, α-guanidino(p-hydroxyphenyl)acetamido, α-acetylureido(p-hydroxyphenyl)acetamido, phenoxyacetamido, o-hydroxyphenoxyacetamido, m-hydroxyphenoxyacetamido, p-hydroxyphenoxyacetamido, methoxyacetamido, ethoxyacetamido, α-amino(p-hydroxy)phenoxyacetamido, α-aminophenoxyacetamido, α-acetylphenoxyacetamido, α-acetyl(p-hydroxy)-phenylacetamido, α-hydroxyphenoxyacetamido, α-hydroxy(p-hydroxy)-phenylacetamido, α-carboxyphenoxyacetamido and esters thereof such as the methylphenyl, indanyl and phenyl esters, α-carboxy(p- hydroxy)phenoxyacetamido and esters thereof such as the methylphenyl, indanyl and phenyl esters, phenoxypropionamido, phenoxybutyramido, benzamido, 2,6-dimethoxybenzamido, 2-ethoxy-1-naphthamido, 2-methoxy-1-naphthamido, 2-propoxy-1-naphthamido, 3-phenyl-5-methyl-4-isoxazolylcarboxamido, 3-o-chlorophenyl-5-methyl-4-isoxazolylcarboxamido, 3-o,o-dichlorophenyl-5-methyl-4-isoxazolylcarboxamido, isothiazolylcarboxamido, 3-o,o-fluorochlorophenyl-5-methyl-4-isoxazolylcarboxamido, 3-phenyl-4-isoxazolylcarboxamido, 3-o-chlorophenyl-4-isoxazolylcarboxamido, 3-o,o-dichlorophenyl-4-isoxazolylcarboxamido, 3-o,o-fluorochlorophenyl-4-isoxazolylcarboxamido, 1-aminocyclohexyl-1-carboxamido, phenylthioacetamido, phenylthiopropionamido, p-hydroxyphenylthioacetamido.

When the group W is other than hydrogen, antibacterially effective compounds are those when W represents methoxy and T represents a group of formula (i) wherein $A_5$ is phenyl, hydroxyphenyl or thienyl, n and m are zero, and X is a carboxy group or a salt or ester or a sulpho group.

Preferred groups U are hydroxy, $C_{1-6}$ alkoxy, such as methoxy, $C_{1-6}$ alkoxy-($C_{1-6}$) alkoxy, such as methoxymethoxy, amino, $C_{1-6}$ alkylamino, such as methyl amino, ethylamino, n- and iso-propylamino, n-, sec-, tert- and iso-butylamino.

The group $R^3$ represents hydrogen or an organic group linked through a sulphur or carbon atom. For example $R^3$ may represent a group of formula $R^a$ or $SR^a$ where $R^a$ is hydrogen or an optionally substituted $C_{1-10}$ hydrocarbon or heterocyclic group. Preferably, $R^3$ represents hydrogen, optionally substituted $C_{1-10}$ alkyl or optionally substituted $C_{1-10}$ alkylthio, wherein the substituent is hydroxy, $C_{1-6}$ alkoxy, $C_{1-6}$ alkanoyloxy, halogen, mercapto, $C_{1-6}$ alkylthio, heterocyclicthio, amino, mono- or dialkylamino, alkanoylamino, carboxy, or $C_{1-6}$ alkoxycarbonyl.

This invention also provides a pharmaceutical composition which comprises a pharmaceutically acceptable carrier and a biologically active 1-aza[3.2.0]bicycloheptan-2-carboxylic acid or a pharmaceutically acceptable salt or in vivo hydrolysable ester thereof, having a substituent at position 7 of the formula $=CR^1R^2$ wherein $R^1$ and $R^2$ are as hereinbefore defined.

Such compositions are normally provided in unit dose form containing from 50 to 500 mg or more usually from 100 to 250 mg of a compound of this invention.

The compositions of this invention are usually adapted for administration to animals including humans. Such compositions may be formulated in a conventional manner for antibacterial agents, for example in a similar manner to that known from penicillins and cephalosporins.

The compounds of this invention may be provided in orally administrable form, for example as tablets or capsules. The compounds of this invention may be provided in a form suitable for administration by injection or infusion, for example in the form of a sterile salt such as the sterile sodium salt sealed in a vial ampoule.

It is believed that infections most readily treated by the compounds of this invention are those due to strains of Bacillus, Staphylococcus and Streptococcus.

The compounds of this invention may be prepared by: (a) reacting a 1-aza[3.2.0]bicycloheptan-2-carboxylic acid or a salt or ester thereof, with a compound of formula (IV) or (V):

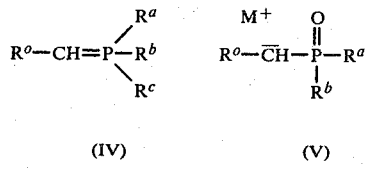

wherein $R^o$ is an electron withdrawing group $R^a$, $R^b$ and $R^c$ are the same or different and each is $C_{1-6}$ alkyl, aryl, or aralkyl; and $M^+$ represents a metal ion;

(b) optionally converting the group $R^o$ to a different group $R^1$; and (c) for compounds in which $R^2$ is not hydrogen, replacing the hydrogen by a group $R^2$.

The reaction with a compound of formula (IV) or (V) is usually carried out in an inert solvent such as toluene, xylene, benzene, tetrahydrofuran, or dioxan, at an elevated temperature such as over 50° C., suitably over 100° C., preferably from 100°–200° C.

Suitable metal ions $M^+$ include alkali metal ions, such as sodium or lithium.

Suitable groups $R^o$ include $C_{1-6}$ alkoxycarbonyl, cyano or $C_{1-6}$ alkylcarbonyl.

The compounds of this invention are primarily useful as chemical intermediates, in particular for carrying out reactions which cannot readily be carried out on the unsubstituted β-lactam compound. Some reactions, although they can be carried out on the unsubstituted β-lactam, proceed in improved yields with the compounds of this invention.

Examples of reactions which may advantageously be carried out employing the compounds of this invention include:

1. Carboxylic ester hydrolysis
2. Acylation of 6-amino penicillanic acids and derivatives thereof
3. Functional group modifications, such as:
    (a) C-9 displacement reactions in clavulanic acid derivatives;
    (b) C-6 displacement reactions in clavulanic acid derivatives;
    (c) Introduction of 6α-substituents, such as 6-methoxy, into a penicillanic acid nucleus;
    (d) Modification of the 6α-substituent in a 6α-substituted penicillanic acid derivative, for example conversion of 6-methylthio to 6-methoxy.

After the reaction carried out on the compounds of the invention, the substituent at position may be cleared to regenerate the 7-oxo substituent, for example by treatment with ozone in conventional manner.

The following Examples illustrate the preparation and utility of the compounds of the present invention.

EXAMPLE 1

Benzyl(2R,5R)-Z-3(β-phthalimidoethylidene)-Z-7-methoxycarbonylmethylene-4-oxa-1-azabicyclo[3.2.0]heptan-2-carboxylate

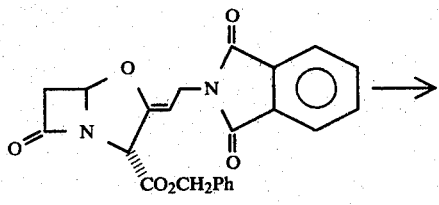

(1)

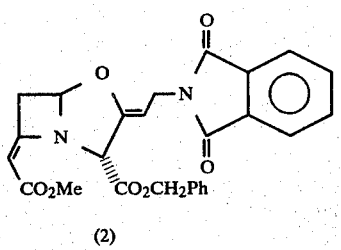

(2)

The phthalimido-clavam (I) (80 mg, 0.19 mmol) and methoxycarbonylmethylene triphenylphosphorane (65 mg, 0.19 mmol) were refluxed together in toluene (3 ml) for 18 hours.

The solvent was removed in vacuo and the residue chromatographed on silica gel eluting with ethyl acetate/cyclohexane (1:3) to afford (2) as an oil (56 mg, 62%).

$\nu_{max}$ (CHCl$_3$) 1760, 1740, 1710, 1660, 1390, 1160 cm$^{-1}$.

δ (CDCl$_3$) 2.69 (1H, d, J 7 Hz, C(6)H̲), 3.08 (1H, dd, J 7 and 2 Hz, C(6)H̲), 3.58 (3H, s, OCH$_3$), 4.35 (2H, d, J 7 Hz, C(9)H̲), 4.78 (1H, t, J 7 Hz, C(8)H̲), 5.06 (1H, s, vinyl H), 5.21 (2H, s, OCH$_2$), 5.29 (1H, s, C(2)H̲), 5.79 (1H, d, J 2 Hz, C(5)H̲), 7.30 (5H, s, Arom.H̲), 7.78 (4H, s, Arom. H̲) ppm.

EXAMPLE 2 p-Bromobenzyl (2R,5R)-Z-3-(β-phthalimidoethylidene)-Z-7-methoxycarbonylmethylene-4-oxa-1-azabicyclo[3.2.0]heptan-2-carboxylate

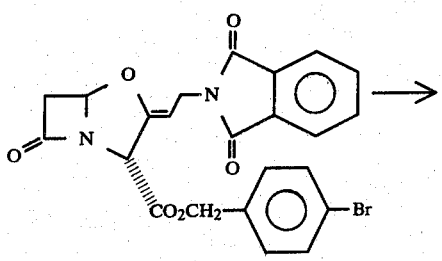

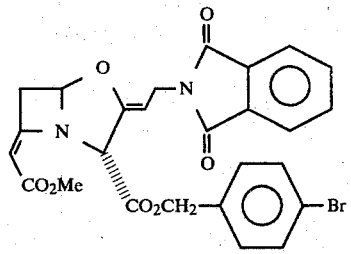

The p-bromobenzyl ester corresponding to compound (1), (278 mg, 0.56 mmol) and phosphorane (188 mg, 0.56 mmol) in toluene (10 ml) were refluxed for 18 hrs. Chromatography of the crude product afforded colourless needles (72 mg, 23%), m.p. 144°–145° (from ethyl acetate/petrol).

$\nu_{max}$ (CHCl$_3$) 1770, 1745, 1710, 1665, 1395, 1170 cm$^{-1}$.

δ (CDCl$_3$) 2.89 (1H, d, J=16 Hz, C(6)H̲), 3.22 (1H, dd, J 16 and 3 Hz, C(6)H̲), 3.58 (3H, s, OCH̲$_3$), 4.35 (2H, d, J 7 Hz, C(9)H̲), 4.77 (1H, t, J 7 Hz, C(8)H̲), 5.05 (1H, s, vinyl H̲), 5.13 (2H, s, OCH$_2$), 5.29 (1H, s, C(2)H̲), 5.76 (1H, d, J 3 Hz, C(5)H̲), 7.15 (2H, d, J 8 Hz, Aryl H̲), 7.40 (2H, d, J 8 Hz, Aryl H̲), 7.63–7.88 (4H, complex, Aryl H̲) ppm.

EXAMPLE 3

Benzyl (2R,5R)-Z-3-[β-(dibenzyloxycarbonylamino)ethylidene]-Z-7-methoxycarbonylmethylene-4-oxa-1-azabicyclo[3.2.0]heptan-2-carboxylate

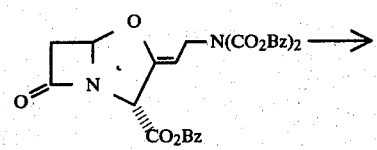

(3)

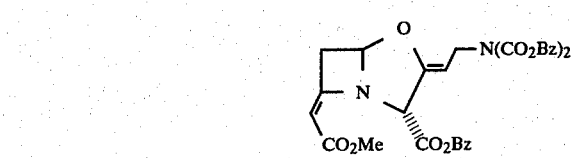

(4)

The tribenzylester (225 mg, 0.405 mmol) and methoxycarbonylmethylene triphenylphosphorane (136 mg, 0.405 mmol) were refluxed in toluene (2 ml) for 18 hrs.

The toluene was removed in vacuo and the residue chromatographed on silica gel, eluting with ethyl acetate/cyclohexane, (1:4) to afford a crude sample of the product (4). A crystalline impurity was present in this sample and this was removed by crystallisation from ethylacetate/petrol to afford pure (4) as a yellow oil (315 mg, 28%).

$\nu_{max}$ (CHCl$_3$) 1740, 1710, 1660, 1170, 1100 cm$^{-1}$.

δ (CDCl$_3$) 2.59 (1H, d, J 16 Hz, C(6)H̲), 3.03 (1H, dd, J 16 and 3 Hz, C(6)H̲), 3.57 (3H, s, OCH̲$_3$), 4.38 (2H, d, J 7 Hz, C(9)H), 4.65 (1H, t, J 7 Hz, C(8)H̲), 4.98 (1H, s, vinyl H̲), 5.16 (6H, s, OCH$_2$), 5.20 (1H, s, C(2)H obscured), 5.47 (1H, d, J 3 Hz, C(5)H̲), 7.30 (15H, s, Aryl H̲) ppm.

EXAMPLE 4

Benzyl (2R,5R)-Z-3-(β-hydroxyethylidene)-Z-7-methoxycarbonylmethylene-4-oxa-1-azabicyclo[3.2.0]heptan-2-carboxylate

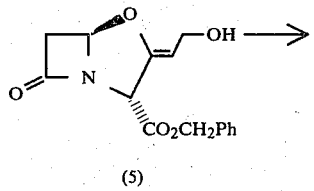

(5)

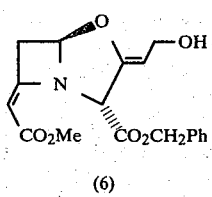

(6)

Benzyl clavulanate (5) (2.89 g, 10.0 mmol) and methoxycarbonylmethylene triphenylphosphorane (3.35 g, 10.0 mmol) were refluxed in toluene (40 ml) for 18 hrs. After this time the solution had darkened considerably.

The crude product was chromatographed on silica gel, eluting with ethyl acetate/cyclohexane (1:3→1:2) to afford the compound (6) as a colourless oil (234 mg, 7%).

$v_{max}$ (CHCl$_3$) 1745, 1710, 1665, 1170 cm$^{-1}$.

δ (CDCl$_3$) 2.14 (1H, broad s, OH), 2.80 (1H, ddd, J 17, 1.5 and 1.0 Hz, C(6)H), 3.17 (1H, ddd, J 17, 3.1 and 1.4 Hz, C(6)H), 3.56 (3H, s, OCH$_3$), 4.16 (2H, d, J 7 hz, C(9)H), 4.83 (1H, dt, J 7 and 0.9 Hz, C(8)H), 5.02 (1H, dd, J 1.4 and 1.5 Hz, vinyl H), 5.20 (2H, s, OCH$_2$), 5.29 (1H, d, J 0.9 Hz, C(2)H), 5.69 (1H, dd, J 3.1 and 1.0 Hz, C(5)H), 7.33 (5H, s, Aryl H) ppm.

$v_{max}$ (EtOH) 258 (ε=11,300) nm.

EXAMPLE 5

Benzyl (2S,5R,6R)-3,3-dimethyl-7-methoxycarbonylmethylene-6-phenoxyacetamido-4-thia-1-azobicyclo[3.2.0-]heptan-2-carboxylate

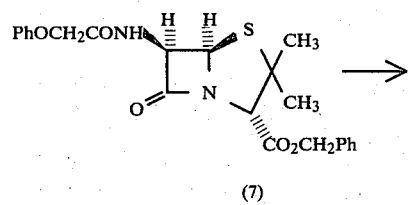

(7)

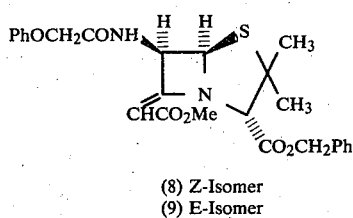

(8) Z-Isomer
(9) E-Isomer

Penicillin V benzyl ester (7) (2.20 g, 5.0 mmol) and methoxycarbonylmethylene triphenylphosphorane (1.76 g, 5.25 mmol) were refluxed in toluene (35 ml) for 18 hrs. Chromatography on silica gel eluting with ethyl acetate/cyclohexane (1:3) afforded (8) as a colourless gum (1.43 g, 58%);

Z-Isomer $v_{max}$ (CHCl$_3$) 1745, 1700, 1690, 1660, 1220 cm$^{-1}$.

δ (CDCl$_3$) 1.35 (3H, s, CH$_3$), 1.57 (3H, s, CH$_3$), 3.57 (3H, s, OCH$_3$), 4.51 (2H, s, OCH$_2$CO), 4.98 (1H, s, C(2)H), 4.99 (1H, d, J 0.5 Hz approx. vinyl H), 5.21 (2H, s, OCH$_2$), 5.42 (1H, ddd, J 9, 5 and 0.5 Hz, C(6)H), 5.78 (1H, d, J 5 Hz, C(5)H), 6.85–7.35 (1OH, aryl H), approx. 7.3 (1H, d, J 9 Hz, NH) ppm.

λ$_{max}$ (EtOH) 270 (ε=13,000) nm.

Continued elution gave (9) as a colourless gum 1.04 g, 42%).

E-Isomer $v_{max}$ (CHCl$_3$) 1745, 1700, 1690, 1660, 1240, 1150 cm$^{-1}$.

δ (CDCl$_3$) 1.35 (3H, s, CH$_3$), 1.60 (3H, s, CH$_3$), 3.60 (3H, s, OCH$_3$), 3.91 (1H, s, C(2)H), 4.50 (2H, s, OCH$_2$CO), 5.09 (1H, d, J 1 Hz, vinyl H), 5.18 (2H, s, OCH$_2$), 5.43 (1H, ddd, J 5, 5 and 1 Hz, C(6)H), 5.81 (1H, d, J 5 Hz, C(5)H), 6.86–7.35 (1OH, Aryl H), 7.92 (1H, d, J 5 Hz, NH) ppm.

λ$_{max}$ (EtOH) 269 (ε=17,800) nm.

EXAMPLE 6

Benzyl 6β-phenoxyacetamidopenicillanate by ozonolysis of products of Example 5

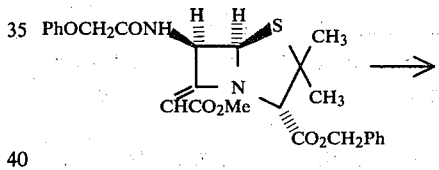

(8) Z-Isomer
(9) E-Isomer

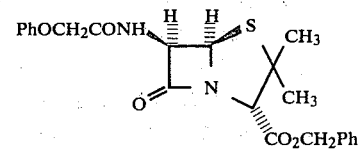

(7)

The diester (8) (168 mg, 0.34 mmol) in ethyl acetate (20 ml) was stirred and cooled to −70°. Ozonised oxygen was passed through the stirred solution for approximately 5 mins until a faint blue colour was just detectable. Argon was then bubbled through the cooled solution for 30 mins.

Triphenylphosphine (89 mg, 0.34 mmol) was then added and the solution allowed to warm to room temperature. Stirred at 20° for 1 hour.

Evaporated solvent to afford an oil which was chromatographed on silica gel, eluting with ethyl acetate/cyclohexane (1:3) to afford Penicillin V benzyl ester (7) as a white solid (142 mg, 95%). I.r. and n.m.r. spectra were identical to those of an authentic sample.

Similarly the E-isomer (9) (191 mg, 0.39 mmol) in ethyl acetate (25 ml) afforded (7) (117 mg, 69%) on ozonolysis in an identical manner.

EXAMPLE 7

Lithium (2S,5R,6R)-3,3-dimethyl-E-7-methoxycarbonylmethylene-6-phenoxyacetamido-4-thia-1-azabicyclo[3.2.0]heptan-2-carboxylate

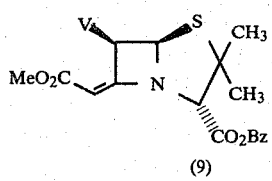

The diester (9) (26 mg) in tetrahydrofuran (20 ml) was hydrogenated over 10% Pd/C (35 mg) for 5–6 hrs at ambient temperature and pressure. The mixture was filtered through celite and some of the THF evaporated in vacuo. Added an equal volume of water and titrated the resulting suspension to pH 7.0 with dil. lithium hydroxide solution. The solvents were removed in vacuo.

The resulting oil was triturated with ether containing a little acetone, to afford lithium salt as a white solid (13 mg, 60%).

δ (D$_2$O) 1.36 (3H, s, CH$_3$), 1.52 (3H, s, CH$_3$), 3.49 (3H, s, OCH$_3$), 3.73 (1H, s, C(2)H), 5.06 (1H, s, vinyl H), 5.46 (1H, d, J 5 Hz, C(6)H), 5.66 (1H, d, J 5 Hz, C(5)H), 6.85–7.08 (3H, complex, Aryl H), 7.20–7.38 (2H, Aryl H) ppm.

λ$_{max}$ (H$_2$O) 274 (ε=18,500) nm.

EXAMPLE 8

(a) Benzyl (2S,5R,6S)-3,3-dimethyl-6-methoxy-E-7-methoxycarbonylmethylene-6-phenoxyacetamido-4-thia-1-azabicyclo[3.2.0]heptan-2-carboxylate

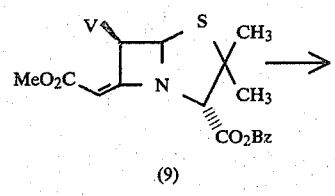

A solution of analar methanol (0.053 ml, 1.55 mmol) in dry THF (40 ml) was cooled, under nitrogen, to −70°. A solution of n-butyl lithium (1.55 mmol) in hexane was then added and stirring continued at −70° for 20 mins.

The diester (9) (221 mg, 0.445 mmol) in dry THF (5 ml) was now added dropwise but rapidly to the lithium methoxide solution. After 1 minute a solution of t-butyl hypochlorite (58 mg, 20% excess) in dry THF (2 ml) was added rapidly and stirring at −70° continued for a further 15 mins.

Glacial acetic acid (1 ml) was now added and the reaction mixture allowed to reach room temperature. Extraction with ethyl acetate and thorough washing with water afforded a crude extract which was chromatographed on silica gel eluting with ethyl acetate-cyclohexane (1:3). The desired product was obtained as an oil (38 mg, 16%).

ν$_{max}$ (CHCl$_3$) 3300, 1740, 1690, 1650, 1600, 1150, 1080 cm$^{-1}$.

δ (CDCl$_3$) 1.26 (3H, s, CH$_3$), 1.33 (3H, s, CH$_3$), 3.41 (3H, s, OCH$_3$), 3.68 (3H, s, COOCH$_3$), 3.88 (1H, s, C(2)H), 4.52 (2H, s, CH$_2$CO), 5.06 (1H, s, vinyl H), 5.20 (2H, s, OCH$_2$), 5.75 (1H, s, C(5)H), 6.90–7.35 (1OH, Arom. H), 9.65 (1H, broad s, NH) ppm.

λ$_{max}$ (EtOH). 276 (ε=13,200) nm.

(b) Benzyl 6α-methoxy-6β-phenoxyacetamidopenicillanate

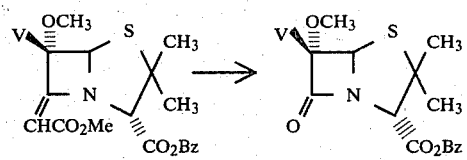

The methoxy compound (34 mg, 0.065 mmol) in ethyl acetate (10 ml) was stirred at −70° and ozone passed slowly through the solution until a pale blue colour was detected. Argon was then passed through the solution for approx. 1 hr. at −70°. Triphenylphosphine (20 mg) was now added and the solution allowed to reach room temperature. Stirring was continued for a further 1 hour and the solvent evaporated to give an oil. Chromatography on silica gel, eluting with ethyl acetate/cyclohexane (1:4) gave benzyl 6α-methoxypenicillanate V as an oil (10 mg, 33%). I.r. and n.m.r. identical to authentic sample.

EXAMPLE 9

Benzyl (2S,5R,6R)-6-amino-3,3-dimethyl-7-methoxycarbonylmethylene-4-thia-1-azabicyclo[3.2.0]heptan-2-carboxylate

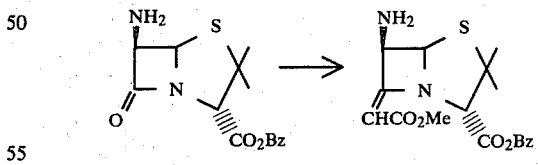

A solution of 6-APA benzyl ester (6.06 g, 19.8 mmol) and methoxycarbonylmethylenetriphenylphosphorane (8.40 g, 25 mmol) in toluene (100 ml) was stirred at reflux for 18 hrs. The solvent was then evaporated under reduced pressure and the residue chromatographed on silica gel. Elution with ethyl acetate/cyclohexane (1:2) gave the desired product as a yellow oil (1.14 g, 19%).

ν$_{max}$ (CHCl$_3$) 1730, 1700, 1645 cm$^{-1}$.

δ (CDCl$_3$) 1.40 (3H, s, CH$_3$), 1.68 (3H, s, CH$_3$), 2.15 (2H, broad s, NH$_2$), 3.66 (3H, s, OCH$_3$), 3.90 (1H, s, C(2)H), 4.57 (1H, d, J 5 Hz, C(6)H), 5.00 (1H, s, vinyl H), 5.20 (2H, s, CH$_2$Ph), 5.76 (1H, d, J 5 Hz, C(5)H), 7.38 (5H, s, aryl H) ppm.

EXAMPLE 10

Benzyl (2S,5R,6R)-6-(2-benzyloxycarbonyl-2-thien-3'-ylacetamido)-3,3-dimethyl-7-methoxycarbonylmethylene-4-thia-1-azabicyclo[3.2.0]heptan-2-carboxylate

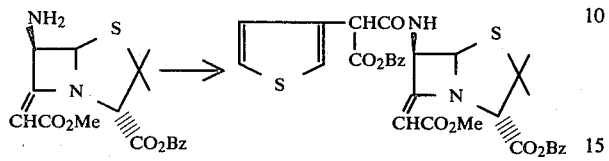

A solution of the 6-APA derivative (0.89 g, 2.46 mmol) in dry tetrahydrofuran (50 ml) was stirred at 0° during the addition of triethylamine (0.50 g, 5.0 mmol) followed by benzyl (3'-thienyl)malonyl chloride (1.47 g, 5.0 mmol). After stirring for 1 hr. the reaction mixture was diluted with ethyl acetate and washed with saturated sodium bicarbonate solution. The organic layer was dried (MgSO$_4$) and the solvent evaporated under reduced pressure. The crude product was chromatographed on silica gel eluting with ethyl acetate/cyclohexane (1:4) to give desired product as a mixture of diastereoisomers (1.04 g, 68%).

$\nu_{max}$ (CHCl$_3$) 1740, 1700, 1650 cm$^{-1}$.

δ (CDCl$_3$) 1.33 (3H, s, CH$_3$), 1.57 (3H, s, CH$_3$), 3.57 and 3.58 (3H, s, OCH$_3$), 3.90 (1H, s, C(2)H), 4.75 (1H, s, malonyl CH), 5.00 (1H, vinyl H), 5.22 (4H, s, CH$_2$Ph), 5.70–5.80 (2H, overlapping m, C(5)H and C(6)H), 7.35 (13H, aryl H), 7.75 (1H, d, J 5 Hz, NH) ppm.

EXAMPLE 11

Benzyl 6β-(2-benzyloxycarbonyl-2-thien-3'-ylacetamido)-penicillanate

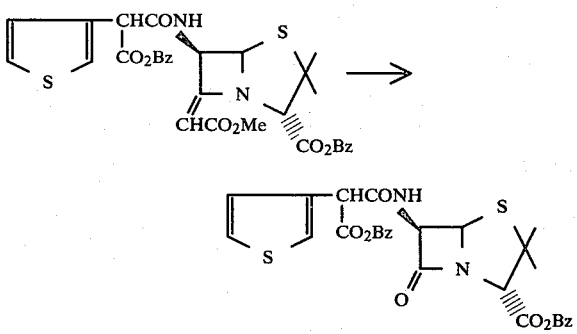

A solution of the acylamino compound (0.41 g, 0.66 mmol) in ethyl acetate (20 ml) was cooled (−70°) and ozonised oxygen passed through the solution for approx. 5 mins. The system was then flushed with argon for 30 mins. and triphenylphosphine (350 mg) added. The solution was then stirred for 1 hr at room temperature.

Evaporation of the solvent afforded an oil which was chromatographed on silica gel. Elution with ethyl acetate/cyclohexane (1:4) gave the desired β-lactam as a colourless oil (180 mg, 49%).

$\nu_{max}$ (CHCl$_3$) 1790, 1740, 1730, 1680 cm$^{-1}$.

δ (CDCl$_3$) 1.35, 1.45 and 1.51 (6H, CH$_3$), 4.40 and 4.43 (1H, s, C(3)H), 4.71 and 4.74 (1H, s, malonyl, CH), 5.14 (4H, s, CH$_2$Ph), 5.45–5.65 (2H, overlapping m, C(5)H and C(6)H), 7.25 and 7.32 (13H, aryl H), 7.58 (1H, d, J 8 Hz, NH) ppm.

EXAMPLE 12

Lithium (2S,5R,6R)-3,3-dimethyl-E-7-methoxycarbonylmethylene-6-phenoxyacetamido-4-thia-1-azabicyclo[3.2.0]heptan-2-carboxylate

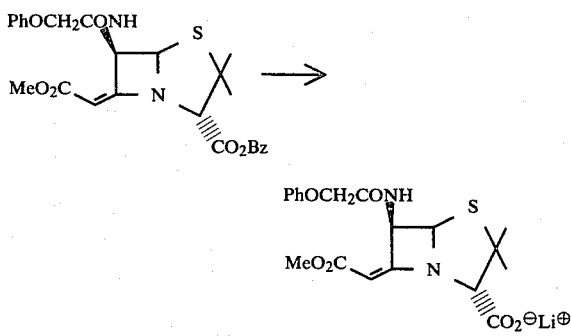

A solution of the benzyl ester (0.27 g, 0.545 mmol) in aqueous tetrahydrofuran (10 ml, 1:1) was stirred at 20° during the addition of 1M lithium hydroxide solution. The pH of the solution was kept at 13.0 for 2 hrs. After this time the solution was neutralised to pH 7.0 by addition of dil. hydrochloric acid and the solvents evaporated under reduced pressure. The residue was partitioned between ethyl acetate and water and the aqueous layer re-evaporated.

Chromatography on silica gel, eluting with n-butanol/ethanol/water (4:1:1) afforded the desired product as a pale solid (110 mg, 50%).

EXAMPLE 13

Benzyl (2S,5R,6R)-7-cyanomethylene-3,3-dimethyl-6-phenoxyacetamido-4-thia-1-azabicyclo[3.2.0]heptan-2-carboxylate

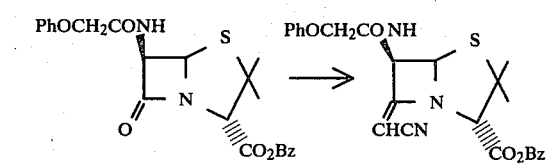

A solution of the penicillin (357 mg, 0.81 mmol) and cyanomethylenetriphenylphosphorane (270 mg, 0.90 mmol) in toluene (30 ml) was heated under reflux for 18 hrs. The reaction mixture was then cooled and the solvent evaporated under reduced pressure. The residue was chromatographed on silica gel eluting with ethyl acetate/cyclohexane (1:4) to afford recovered starting material (71 mg, 20%) followed by the Z-isomer of the desired product as a colourless oil (190 mg, 51%).

$\nu_{max}$ (CHCl$_3$) 2210, 1740, 1685, 1660, 1600 cm$^{-1}$.

δ (CDCl$_3$) 1.35 (3H, s, CH$_3$), 1.60 (3H, s, CH$_3$), 4.42 (1H, d, J 1 Hz, vinyl H), 4.50 (2H, s, OCH$_2$CO), 4.65 (1H, s, C(2)H), 5.10 and 5.25 (2H, AB quartet, J 12 Hz, CH$_2$Ph), 5.40 (1H, td, J 8.5, 4.5 and 1 Hz, C(6)H), 5.79 (1H, d, J 4.5 Hz, C(5)H), 6.85–7.35 (11H, aryl H and NH) ppm.

Continued elution provided the E-isomer as a colourless oil (102 mg, 27%).

$\nu_{max}$ (CHCl$_3$) 2210, 1740, 1685, 1660, 1600 cm$^{-1}$.

δ (CDCl$_3$) 1.35 (3H, s, CH$_3$), 1.60 (3H, s, CH$_3$), 3.87 (1H, s, C(2)H), 4.47 (1H, d, J 1 Hz, vinyl H), 4.43 and 4.65 (2H, AB quartet, J 16 Hz, OCH$_2$CO), 5.17 (2H, s, CH$_2$Ph), ca. 5.70 (2H, overlapping m, C(5)H and C(6)H), 6.90-7.35 (11H, aryl H and NH) ppm.

EXAMPLE 14

Benzyl (2R,5R)-Z-3-(β-dichloroacetoxyethylidene)-Z-7-methoxycarbonylmethylene-4-oxa-1-azabicyclo[3.2.0-]heptan-2-carboxylate

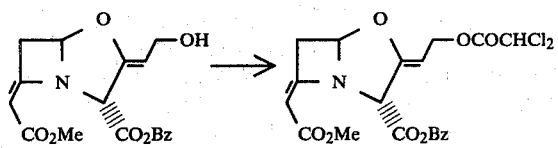

A solution of the hydroxy-compound (181 mg, 0.53 mmol) in dichloromethane (5 ml) was stirred and cooled to 0°. Pyridine (0.043 ml, 42 mg, 0.53 mmol) was added followed by dichloroacetyl chloride (0.050 ml, 78 mg, 0.53 mmol) and stirring at 0° maintained for a further 30 mins.

The reaction mixture was diluted with dichloromethane and washed successively with citric acid solution, water and brine to afford, after evaporation of the solvent, the desired product as an oil (260 mg).

$\nu_{max}$ (CHCl$_3$) 1740, 1700, 1660 cm$^{-1}$.

δ (CDCl$_3$) 2.87 (1H, d, J 17 Hz, C(6)H), 3.23 (1H, dd, J 17 and 3 Hz, C(6)H), 3.60 (3H, s, OCH$_3$), 4.82 (3H, C(8)H and C(9)H), 5.08 (1H, t, J 1 Hz, vinyl H), 5.22 (2H, s, CH$_2$Ph), 5.38 (1H, s, C(2)H), 5.77 (1H, d, J 3 Hz, C(5)H), 5.89 (1H, s, CHCl$_2$), 7.35 (5H, s, aryl H) ppm.

EXAMPLE 15

Benzyl (2R,5R)-Z-3-(β-diethylaminoethylidene)-Z-7-methoxycarbonylmethylene-4-oxa-1-azabicyclo[3.2.0]heptan-2-carboxylate

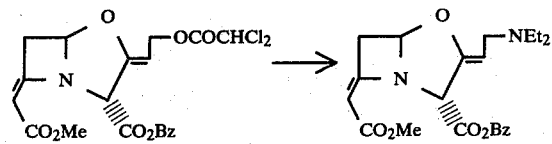

A solution of the dichloroacetate (260 mg, 0.53 mmol) in dimethylformamide (5 ml) was treated with diethylamine (0.11 ml, 78 mg, 1.06 mmol) and stirred at room temperature for 2 hours. The solution was diluted with ethyl acetate and washed with water. After drying (MgSO$_4$) the solvent was evaporated to afford an oil which was chromatographed on silica gel. Elution with ethyl acetate/methanol (1:1) provided the desired product as a yellow oil (108 mg, 51%).

$\nu_{max}$ (CHCl$_3$) 1740, 1700, 1660, 1620 cm$^{-1}$ δ (CDCl$_3$) 1.00 (6H,t,J7 Hz,CH$_2$CH$_3$), 2.43 (4H,q,J,7 Hz,CH$_2$CH$_3$), 2.78 (1H,d,J17 Hz,C(6)H), 3.20 (1H,dd,J17 and 3 Hz, C(6)H), 3.25 (2H,d,J7 Hz,C(9)H), 3.59 (3H,s,OCH$_3$), 4.69 (1H,t,J7 Hz,C(8)H), 5.05 (1H,t,J0.5 Hz, vinylH), 5.22 (2H,s,CH$_2$Ph), 5.30 (1H,s, C(2)H), 5.71 (1H,d,J3 Hz,C(5)H), 7.33 (5H,s,arylH)ppm.

EXAMPLE 16

Benzyl (2R,5R)-Z-3-(β-cyanoethylidene)-Z-7-methoxycarbonylmethylene-4-oxa-1-azabicyclo[3.2.0]heptan-2-carboxylate

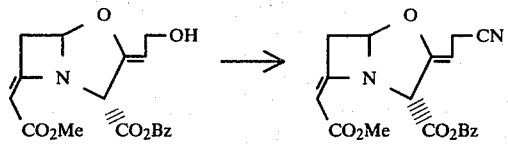

A solution of the hydroxy-compound (217 mg, 0.63 mmol) in ethyl acetate (5 ml) was stirred and cooled to −60°. Pyridine (0.068 ml, 0.84 mmol) was added followed by thionyl chloride (0.055 ml, 0.76 mmol) and the resulting suspension allowed to warm to 20° over the next 30 mins.

The suspension was diluted with ether and washed with 10% citric acid solution, saturated sodium bicarbonate solution and finally with water. Evaporation of the solvent (after drying over MgSO$_4$) afforded the chloro derivative as an unstable oil.

The crude chloro derivative (0.63 mmol) was dissolved in dry dimethylformamide (2 ml) and stirred at −10° in the presence of sodium cyanide (60 mg, 1.2 mmol) for 30 mins. The temperature was then allowed to rise to 0° and stirring continued for a further 30 mins.

The resulting dark solution was diluted with ethyl acetate and washed with water. The solution was dried (MgSO$_4$) and evaporated to afford an oil which was chromatographed on silica gel. Elution with ethyl acetate/cyclohexane (1:4) gave the desired product as a white solid (82 mg, 37%).

$\nu_{max}$ (CHCl$_3$) 2250, 1740, 1700, 1660 cm.$^{-1}$ δ (CDCl$_3$) 2.84 (1H,d,J17 Hz, C(6)H), 3.08 (2H,d,J7 Hz,C(9)H), 3.25 (1H,dd,J17 and 3 Hz,C(6)H), 3.60 (3H,s,OCH$_3$), 4.57 (1H,t, J7 Hz,C(8)H), 5.07 (1H,t,J0.5 Hz vinylH), 5.23 (2H,s,CH$_2$Ph), 5.37 (1H,s,C(2)H), 5.76 (1H,d,J3 Hz,C(5)H), 7.34 (5H,s, arylH)ppm.

EXAMPLE 17

Lithium (2R,5R)-Z-3-(β-hydroxyethylidene)-Z-7-methoxycarbonylmethylene-4-oxa-1-azabicyclo[3.2.0]heptan-2-carboxylate

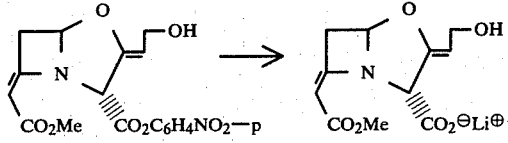

A solution of the p-nitrobenzyl ester (93 mg, 0.24 mmol) in tetrahydrofuran (20 ml) was hydrogenated over 10% palladium on charcoal (30 mg) at ambient temperature and pressure for 15 mins. The suspension was then filtered and the filtrate diluted with an equal volume of water. The stirred solution was then neutralised to pH 7.0 by addition of dilute lithium hydroxide solution and the solvents evaporated under reduced pressure. Trituration of the residue with ether afforded the desired salt as a white solid (42 mg, 67%).

$\nu_{max}$ (KBr) 1700, 1650, 1610 cm.$^{-1}$ δ (D$_2$O) 2.85 (1H,d,J17 Hz,C(6)$\underline{H}$), 3.23 (1H,dd,J17 and 3 Hz,C(6)$\underline{H}$), 3.58 (3H,s,OC$\underline{H}_3$), 4.09 (2H,d, J 7 Hz, C(9)$\underline{H}$), 4.77 (1$\underline{H}$, s,C(2)$\underline{H}$), 4.81 (1H,t,J7 Hz,C(8)$\underline{H}$), 5.01 (1$\underline{H}$,t,J0.5 Hz, vinyl$\underline{H}$), 5.67 (1H,d,J3 Hz,C(5)$\underline{H}$)ppm.

EXAMPLE 18

Sodium (2R,5R)-Z-3-(β-hydroxyethylidene)-Z-7-methoxycarbonylmethylene-4-oxa-1-azabicyclo[3.2.0]heptane-2-carboxylate

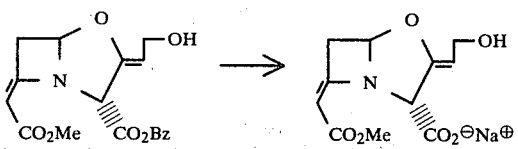

A stirred solution of the benzyl ester (104 mg, 0.30 mmol) in aqueous tetrahydrofuran (20 ml, 1:1) was maintained at pH 12.0–12.5 by addition of 1M sodium hydroxide solution dispensed from an automatic burette. After 1 hour the pH of the solution was brought to 7.0 by addition of dilute hydrochloric acid and the solvents evaporated under reduced pressure.

The residue was chromatographed on silica gel eluting with n-butanol/ethanol/water (4:1:1) to give the desired product as a pale solid (83 mg, 100%)

EXAMPLE 19

Benzyl (2R,5R,6R)-Z-3-(β-hydroxyethylidene)-6-(1'-hydroxypropyl)-Z-7-methoxycarbonylmethylene-4-oxa-1-azabicyclo[3.2.0]heptan-2-carboxylate

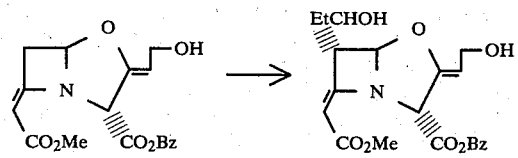

A stirred solution of hexamethyldisilazane (1.77 g, 11.0 mmol) in dry tetrahydrofuran (60 ml) in a nitrogen atmosphere was cooled in −20° and treated with n-butyl lithium (4.6 ml of a 2.4M solution in hexane, 11.0 mmol). The temperature was maintained at −20° for 20 mins. and then allowed to cool to −78°.

A solution of the diester (1.26 g, 3.66 mmol) in dry tetrahydrofuran (10 ml) was now added dropwise, but rapidly, to the cooled solution.

After a further 20 mins. redistilled propionaldehyde (212 mg, 3.66 mmol) in dry tetrahydrofuran (2 ml) was added dropwise to the stirred solution and the temperature maintained at −78° for a further 2 hours.

The reaction was quenched with 10% citric acid solution and the temperature allowed to reach 20°. The resulting mixture was partitioned between ethyl acetate and water. The ethyl acetate layer was washed with water and brine, dried (MgSO$_4$), and evaporated to afford the crude product. Chromatography of this on silica gel eluting with ethyl acetate/cyclohexane (1:2) gave the 7-E isomer of the starting material as an oil (91 mg, 7%).

$\nu_{max}$ (CHCl$_3$) 1740, 1700, 1660, 1600 cm$^{-1}$. δ(CDCl$_3$), 1.90 (1H, broad s, O$\underline{H}$), 3.18 (1H, d, J 17 Hz, C(6)$\underline{H}$), 3.45 (1H, ddd, J 17, 3 and 1 Hz, C(6)$\underline{H}$), 3.65 (3H, s, OC$\underline{H}_3$), 4.22 (2H, m, C(9)$\underline{H}$), 4.56 (1H, s, $\overline{C(2)}\underline{H}$), 4.84 (1H, t, J 7 Hz, C(8)$\underline{H}$), 5.19 (2H, s, OC$\underline{H}_2$Ph), 5.31 (1H, m, vinyl $\underline{H}$), 5.77 (1H, d, J 3 Hz,C(5)$\underline{H}$), 7.36 (5H, s, Aryl $\underline{H}$) ppm.

Further elution afforded recovered starting material (212 mg, 17%) followed by the desired product as a 1:2 mixture of diastereoisomers (212 mg, 14%).

$\nu_{max}$(CHCl$_3$) 3400, 1740, 1700, 1660 cm.$^{-1}$ δ(CDCl$_3$) 0.97 (3H,t,J7 Hz,CH$_2$C$\underline{H}_3$), 1.58 (2H,m,C$\underline{H}_2$CH$_3$), 2.70 (2H, broad, s, O$\underline{H}$), 3.10 (1H,d,J6 Hz,C(6)$\underline{H}$), 3.57 and 3.62 (3H,s,OC$\underline{H}_3$), 3.8 (1H,m,C$\underline{H}$OH), 4.15 (2H,d,J7 Hz,C(9)$\underline{H}$), 4.82 (1H,t,J7 Hz, C(8)$\underline{H}$), 5.05 and 5.15 (1H,d,J1 Hz, vinyl$\underline{H}$), 5.21 (2$\underline{H}$,s,C$\underline{H}_2$Ph), 5.25 (1H,s,C(2)$\underline{H}$), 5.60 and 5.70 (1H,s,C(5)$\underline{H}$), 7.33(5H,s,aryl$\underline{H}$)ppm.

EXAMPLE 20

Sodium (2R,5R,6R)-Z-3-(β-hydroxyethylidene)-6-(1'-hydroxypropyl)-Z-7-methoxycarbonylmethylene-4-oxa-1-azabicyclo[3.2.0]heptan-2-carboxylate

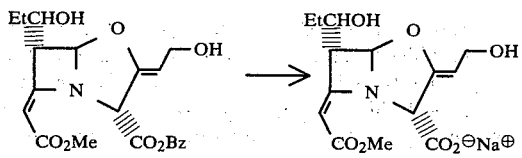

A stirred solution of the benzyl ester (39 mg, 0.097 mmol) in aqueous tetrahydrofuran (ca. 15 ml, 1:1) was maintained at pH 12.0–12.5 for 1 hour by addition of 1M sodium hydroxide dispensed from an automatic burette. After 1 hour the pH of the solution was brought to 7.0 by addition of dilute hydrochlric acid and the solvents evaporated under reduced pressure.

The residue was chromatographed on silica gel eluting with n-butanol/ethanol/water (4:1:1) to afford the desired salt as a pale yellow solid (32 mg, 99%).

$\nu_{max}$ (KBr) 1700, 1660, 1630 cm.$^{-1}$ δ(D$_2$O) 0.92 (3H,t,J7 Hz,CH$_2$C$\underline{H}_3$), 1.57 (2H,m,C$\underline{H}_2$CH$_3$), 3.25 (1H,d,J6 Hz, C($\overline{6}$)$\underline{H}$), 3.65 (3H,s,OC$\underline{H}_3$), 3.8 (1H,m,C$\underline{H}$OH), 4.15 (2H,d,J7 Hz, C(9)$\underline{H}$), 4.80 (1H,t,J$\overline{H}\overline{z}$,C(8)$\underline{H}$), 4.96 (1H,s,C(2)$\underline{H}$), 5.15 and 5.31 (1H,d,J1 Hz, vinyl$\underline{H}$), 5.60 and 5.67 (1H,s,C(5)$\underline{H}$)ppm.

EXAMPLE 21

Benzyl (2S,5R)-Z-7-methoxycarbonylmethylene-3-oxo-4-oxa-1-azabicyclo[3.2.0]heptan-2-carboxylate

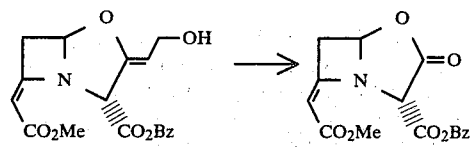

A solution of the benzyl ester (508 mg, 1.47 mmol) in dichloromethane (20 ml) was stirred at −70° and treated rapidly with a saturated (at −70°) solution of ozone in dichloromethane (45 ml, approx 1.8 mmol of ozone) also at −70°. After stirring at this temperature for 15 mins. triphenylphosphine (400 mg) in dichloromethane solution was added. The resulting solution was allowed to reach 20° over the next 1 hour and the solvent then evaporated.

The residue was rapidly chromatographed on silica gel eluting with ethyl acetate/cyclohexane (1:3) to give the desired lactone as an oil (202 mg, 44%).

$\nu_{max}$ (CHCl$_3$) 1810, 1790, 1745, 1700, 1660 cm.$^{-1}$ $\delta$(CDCl$_3$) 3.03 (1H,dd,J17 and 1 HzC(6)H̲), 3.37 (1H,td,J 17, 3 and 1 Hz, C(6)H̲), 3.60 (3H,s,OCH$_3$), 5.17 (2H,s,C(2)H̲ and vinylH̲), 5.28 (2H,s,CH̲$_2$Ph), 5.85 (1H,d, J3 Hz,C(5)H̲), 7.35 (5H,s,arylH̲)ppm.

EXAMPLE 22

Benzyl (2S, 5R, 6R)-3,3-dimethyl-7-benzyloxycarbonylmethylene-6-phenoxyacetamido-4-thia-1-azabicyclo[3.2.0]heptan-2-carboxylate

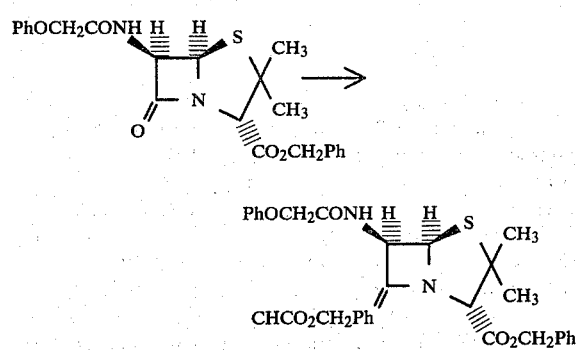

Penicillin V benzyl ester (0.88 g, 2.0 mmol) and benzyloxycarbonylmethylene triphenylphosphorane (1.0 g, 2.4 mmol) in toluene (30 ml) were heated to reflux for 18 hrs. The solution was cooled and the toluene evaporated. The residue was chromatographed on silica gel eluting with ethyl acetate/cyclohexane (1:3) to give the Z-isomer as a crystalline solid (m.p. 85°–86° from ethyl acetate/petrol) (0.39 g, 35%);

Z-isomer $\nu_{max}$ (CHCl$_3$) 1740, 1690, 1660, 1600 cm$^{-1}$. $\delta$ (CDCl$_3$) 1.35 (3H, s, CH̲$_3$), 1.53 (3H, s, CH̲$_3$), 4.50 (2H, s, OCH̲$_2$CO), 5.05 (4H, overlapping, CH̲$_2$Ph,C(2)H̲, vinyl H̲), 5.19(2H, s, CH̲$_2$Ph), 5.41 (1H, ddd, J 9, 5 and 1 Hz, C(6)H̲), 5.79 (1H, d, J 5 Hz, C(5)H̲), 6.85–7.35 (16H, aryl H̲ and NH̲) ppm.

Continued elution gave a 2:1 mixture of E-isomer and starting material (0.56 g).

E-isomer (after further chromatographic purification)

$\nu_{max}$ (CHCl$_3$) 1740, 1690, 1660, 1600 cm$^{-1}$. $\delta$ (CDCl$_3$) 1.32 (3H, s, CH̲$_3$), 1.58 (3H, s, CH̲$_3$), 3.89 (1H, s, C(2)H̲), 4.28 and 4.47 (2H, ABq, J 15 Hz, OCH̲$_2$CO), 5.07 and 5.15 (5H, vinyl H̲ and CH̲$_2$Ph), 5.39 (1H, ddd, J 5, 4 and 1 Hz, C(6)H̲), 5.79 (1H, d, J 4 Hz, C(5)H̲), 6.8–7.35 (15H, aryl H̲), 7.94 (1H, d, J 5 Hz, NH̲) ppm.

EXAMPLE 23

Benzyl (2S, 5R, 6R)-3,3-dimethyl-7-methoxycarbonylmethylene-6-phenylacetamido-4-thia-1-azabicyclo[3.2.0]heptan-2-carboxylate

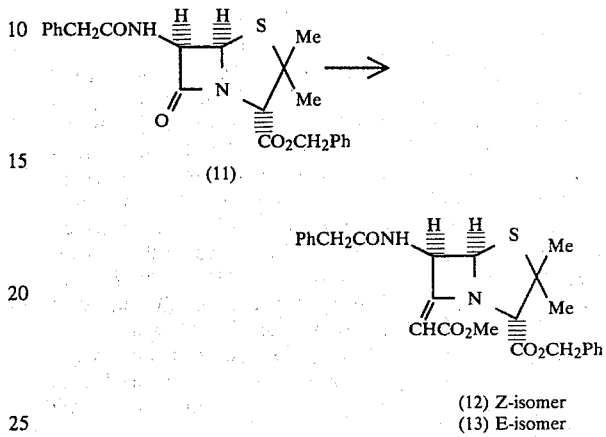

Penicillin G benzyl ester (11) (2.71 g; 6.5 mmol) and methoxycarbonylmethylenetriphenylphosphorane (2.39 g; 7.1 mmol) were refluxed in toluene (35 ml) for 12 h. Chromatography on silica eluting with ethylacetate/hexane mixtures afforded (12) as an amorphous solid (1.06 g, 35%);

Z-isomer $\nu_{max}$ (CHCl$_3$) 1750, 1705, 1680 sh, and 1670 cm$^{-1}$. $\delta$(CDCl$_3$) 1.28 (3H,s), 1.4(3H,s), 3.55(3H,s), 3.57(2H,s), 4.89 (1H,s), 4.9 (1H,d,J ca 1 HZ), 5.18 (2H,s), 5.32 (1H,ddd,J ca 5 and 9 HZ), 5.7 (1H,d,J 5 HZ), 6.1 (1H,d,J 9 HZ), and 7.2–7.5 (10H,m).

Continued elution gave (13) as an amorphous solid (1.26 g, 41%).

E-isomer $\nu_{max}$ (CHCl$_3$) 1750, 1695, and 1660 cm$^{-1}$. $\delta$(CDCl$_3$) 1.32 (3H,s), 1.52 (3H,s), 3.53 (3H,s), 3.56 (2H,s), 3.83 (1H,s), 5.0 (1H,d,J ca 1 HZ), 5.15 (2H,s), 5.3 (1H,ddd,J ca 1 HZ, 4 HZ, and 4.5 HZ), 5.74 (1H,d,J 4 HZ), 6.75 (1H,d,J 4.5 HZ), and 7.2–7.5 (10H,m).

EXAMPLE 24

Benzyl (2S, 5R, 6R)-(Z)-6-Amino-3,3-dimethyl-7-methoxycarbonylmethylene-4-thia-1-azabicyclo[3.2.0]heptane-2-carboxylate (14)

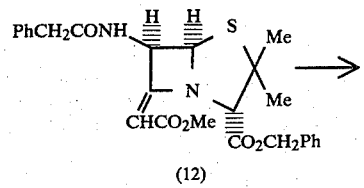

-continued

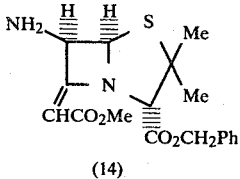
(14)

A solution of the 6-APA derivative (12) (11.50 g) in dry MDC (240 ml) containing N-methylmorpholine (4.87 g) at −25° C. was treated with a solution of phosphorus pentachloride (6.00 g) in dry MDC (~70 ml). The mixture was stirred at 0° C. for 45 min. The mixture was re-cooled to −10° C. and treated with N-methylmorpholine (4.87 g) in dry methanol (125 ml), then allowed to warm to room temperature and stirred a further 2 h. Water (~480 ml) was added to the mixture and stirred vigorously for 20 min. The pH of the mixture was adjusted to 7 with 5N sodium hydroxide solution. The organic phase was washed with water (×2), brine (×1) then dried (MgSO4), filtered and evaporated. Immediate chromatography of the residue on silica gel yielded the product (14) as an amorphous solid (6.60 g).

EXAMPLE 25

Benzyl (2S,5R,6R)-(Z)-6-Benzylideneamino-3,3-dimethyl-7-methoxycarbonylmethylene-4-thia-1-azabicyclo[3.2.0-]heptan-2-carboxylate (15)

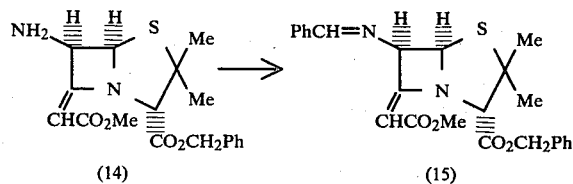

The 6-APA derivative (14) (1.00 g) in toluene (~15 ml) was treated with benzaldehyde (0.29 g) and an excess of anhydrous magnesium sulphate. The mixture was stirred over-night. The mixture was filtered and the filtrate evaporated to yield the crude product (15) (1.20 g); $\nu_{max}$ (CHCl3) 1740, 1700 and 1645 cm$^{-1}$.

EXAMPLE 26

Benzyl (2S,5R,6S)-(Z)-6-Benzylideneamino-3,3-dimethyl-7-methoxycarbonylmethylene-6-methylthio-4-thia-1-azabicyclo[3.2.0]heptan-2-carboxylate (16)

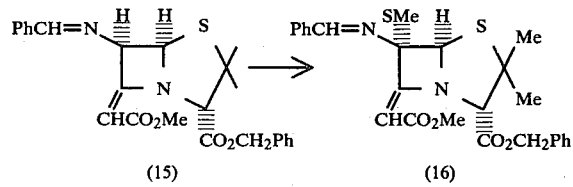

The crude product of example 24 (15) (1.20 g) was dissolved in ethyl acetate (~15 ml) containing methyl methanethiosulphonate (348 mg) and the solution cooled to 0° C. The solution of potassium hydroxide in n-propanol (equivalent to one molecular equivalent of potassium hydroxide) added dropwise. The mixture was stirred at room temperature for 30 min and then poured into water. The organic phase was separated, washed with water (×2), dried, and evaporated. Chromatography of the residue on silica gel gave the product (16), (418 mg); $\nu_{max}$ (CHCl3) 1740, 1705 and 1640 cm$^{-1}$; δppm (CDCl3) (60 MHZ), 1.40 (s, 3H), 1.65(s,3H), 2.28 (s,3H), 3.65 (s,3H), 4.88 (s,1H), 5.05(s,1H), 5.30 (s,2H), 5.90(s,1H), 7.25 to 8.05 (aromatics, 10H), 8.50 (s,1H).

EXAMPLE 27

Benzyl (2S,5R,6S)-(Z)-6-Amino-3,3-dimethyl-7-methoxycarbonylmethylene-6-methylthio-4-thia-1-azabicyclo[3.2.0]heptan-2-carboxylate (17)

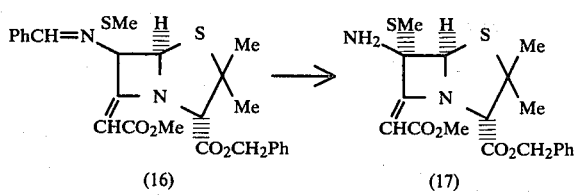

The 6-APA derivative (16) (50 mg) in a small volume of ethyl acetate at 0° C. was treated with p-toluenesulphonic acid monohydrate (19 mg). The solution was stirred for 30 min during which time the temperature rose to ~10° C. The solution was washed with sat. NaHCO3 solution, water (×2) and brine, then dried (MgSO4), filtered and evaporated. Chromatography of the residue on silica gel yielded the product (17) as an oil (30 mg); $\nu_{max}$ (CHCl3) 1740, 1700 and 1650 cm$^{-1}$; δppm (CDCl3) (60 MHz) 1.37 (s,3H), 1.63 (s,3H), 2.07(br s,2H), 2.23(s,3H), 3.63 (s,3H), 5.00 (s,1H), 5.10(s,1H), 5.23(s,2H), 5.67(s,1H), 7.37(s,5H).

EXAMPLE 28

Benzyl (2S,5R,6S)-(Z)-6-(2-Benzyloxycarbonyl-2-thien-3'-yl-acetamido-3,3-dimethyl-6-methoxy-7-methoxycarbonylmethylene-4-thia-1-azabicyclo[3.2.0]heptane-2-carboxylate (19)

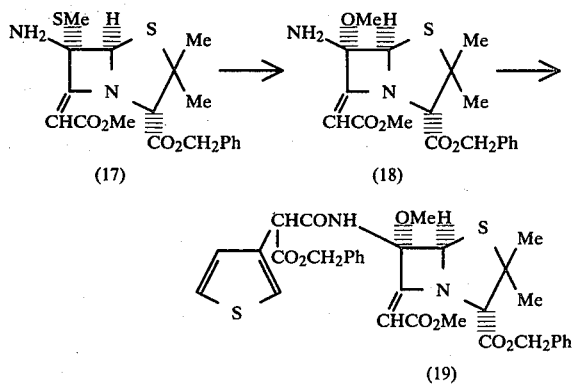

The 6-APA derivative (17) (860 mg) in isopropyl acetate (20 ml) containing methanol (5 ml) was cooled to 0° C. and treated with a solution of silver nitrate (380 mg) in a mixture of pyridine (4 ml) and methanol (8 ml). After ½ h stirring at 0° C. the mixture was filtered through Kieselguhr. The filtrate was washed successively with water, 1% sodium sulphide solution, 0.1% sodium sulphide solution, water (×2), and brine. The solution was dried (MgSO4), filtered and the solvent evaporated off, giving the crude 6-APA derivative (18). The latter (18) was dissolved in dry MDC (40 ml) containing pyridine (250 mg) and the mixture cooled to 0° C. A solution of 2-benzyloxycarbonyl-2-thien-3'-ylacetyl chloride (approx. 808 mg) in dry MDC (8 ml) was added dropwise. The solution was stirred at 0° C. for ½ h then at room temperature for 1½ h. The solution was washed successively with saturated NaHCO$_3$, water, dilute HCl, water and brine. The solution was dried (MgSO$_4$), filtered and the solvent evaporated off. Chromatography of the residue on silica gel yielded the product (19) as a white amorphous solid (970 mg). $\nu_{max}$ (CHCl$_3$) 3325, 1740, 1695 and 1650 cm$^{-1}$; δppm (90 MHZ) 1.25 and 1.30 (both s, together 6H), 3.24 (s,3H), 3.57(s,3H), 4.70(s,1H), 5.06 and 5.08 (both s, together 1H), 5.17(s,4H), 5.29 and 5.32 (both s, together 1H), 5.63(s,1H), 6.95 to 7.60 (m,14H). (Found: M+ 650.1750, C$_{33}$H$_{34}$N$_2$O$_8$S$_2$ requires 650.1754).

EXAMPLE 29

Benzyl 6β-(2-Benzyloxycarbonyl-2-thien-3'-yl acetamido)-6α-methoxypenicillanate (20)

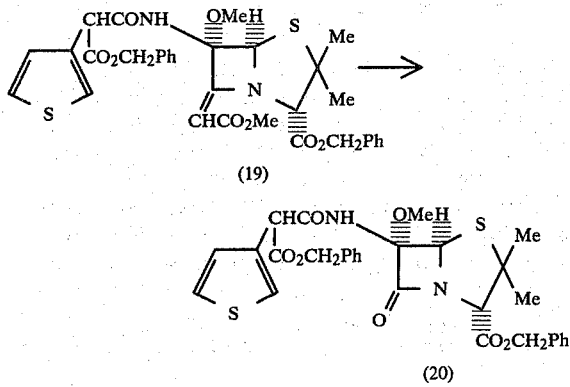

A solution of the 6-APA derivative (19) (150 mg) in dry MDC (4 ml) at −78° C. was treated with a solution of ozone in dry MDC (5.77 ml) (saturated at −78° C.). After 5 min at −78° C., triphenylphosphine (121 mg) in dry MDC (4 ml) was added and the mixture stirred for 20 min. The solution was allowed to warm to RT and the solvent evaporated off. Chromatography of the residue on silica gel yielded the desired product (20) (27 mg). $\nu_{max}$ (CHCl$_3$) 3400, 1775, 1740, and 1690 cm$^{-1}$; δppm (90 MHz) 1.23 and 1.28 (both s, together 6H), 3.31 and 3.36 (both s, together 3H), 4.36 and 4.40 (both s, together 1H), 3.72(s, 1H), 5.14(s,2H), 5.19(s,2H), 5.50 (s,1H) 6.95 to ~7.70 (m, 14H).

I claim:

1. A 1-aza[3.2.0]bicycloheptan-2-carboxylic acid or salt or ester thereof having a substituent at position 7 of the formula:

=CR$^1$R$^2$ wherein R$^1$ and R$^2$ are each hydrogen, halo, a hydrocarbon of 1 to 10 carbon atoms unsubstituted or substituted by hydroxy, carboxy or alkoxycarbonyl of 1 to 6 carbon atoms in the alkoxy moiety, cyano or esterified carboxyl.

2. A compound according to claim 1 wherein R$^1$ is hydrogen.

3. A compound according to claim 1 or 2 wherein R$^2$ is cyano, alkylcarbonyl of 1 to 6 carbon atoms in the alkyl moiety, alkoxycarbonyl of 1 to 6 carbon atoms in the alkoxy moiety, aryloxycarbonyl or aralkoxycarbonyl wherein the aryl moiety is phenyl or phenyl substituted by chloro, bromo, nitro or alkyl of 1 to 6 carbon atoms.

4. A compound according to claim 1 or claim 2 wherein R$^2$ is cyano, alkylcarbonyl of 1 to 6 carbon atoms, or esterified carboxyl.

5. A compound according to claim 1 or claim 2 wherein R$^2$ is alkoxycarbonyl of 1 to 6 carbon atoms or benzyloxycarbonyl.

6. A compound according to claim 1 of the formula (I):

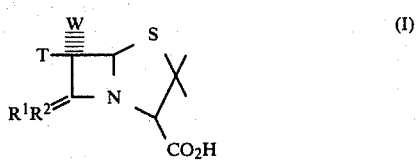

or a salt or ester thereof, wherein R$^1$ and R$^2$ are each hydrogen, halo, a hydrocarbon of 1 to 10 carbon atoms unsubstituted or substituted by hydroxy, carboxy or alkoxycarbonyl of 1 to 6 carbon atoms in the alkoxy moiety, cyano or esterified carboxyl, T is hydrogen, amino or acylamino and W is hydrogen, arylthio, alkylthio of 1 to 6 carbon atoms or methoxy.

7. A compound according to claim 6 wherein T is amino or a group of formula

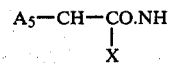

wherein A$_5$ is phenyl, hydroxyphenyl or thienyl and X is sulpho or carboxy or a salt or ester thereof.

8. A compound according to claim 1 of the formula (II):

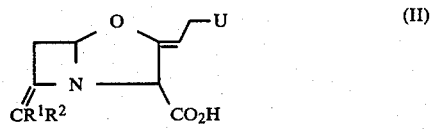

or a salt or ester thereof, wherein R$^1$ and R$^2$ are each hydrogen, halo, a hydrocarbon of 1 to 10 carbon atoms unsubstituted or substituted by hydroxy, carboxy or alkoxycarbonyl of 1 to 6 carbon atoms in the alkoxy moiety, cyano or esterified carboxyl, and U is hydroxyl, substituted hydroxyl, thiol, substituted thio, amino, mono- or di-hydroxycarbyl substituted amino, or mono- or di-acylamino.

9. A compound according to claim 8 wherein U is hydroxyl.

10. A process for the preparation of a compound of claim 1 which comprises reacting a 1-aza[3.2.0]bicycloheptan-2-carboxylic acid or a salt or ester thereof, with a compound of formula (IV) or (V):

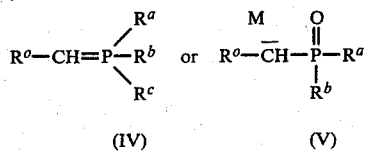

wherein R° is cyano, alkylcarbonyl of 1 to 6 carbon atoms in the alkyl moiety or esterified carboxyl, $R^a$, $R^b$ and $R^c$ are the same or different and each is alkyl of 1 to 6 carbon atoms, aryl, or aralkyl; and $M^+$ is a metal ion;

(a) and optionally thereafter converting the group R° to a different group $R^1$; and (b) for compounds in which $R^2$ is not hydrogen, replacing the hydrogen atom of $R^2$ by a different $R^2$ group.

11. A pharmaceutical composition useful for treating Bacillus, Staphylococcus and Streptococcus infections in animals including humans which comprises a therapeutically effective amount of a compound of the formula (I):

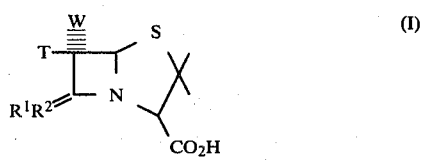

or a pharmaceutically acceptable salt thereof or a pharmaceutically acceptable ester thereof wherein $R^1$ and $R^2$ are each hydrogen, halo, a hydrocarbon of 1 to 10 carbon atoms unsubstituted or substituted by hydroxy, carboxy or alkoxycarbonyl of 1 to 6 carbon atoms in the alkoxy moiety, cyano or esterified carboxyl; T is hydrogen, amino or acylamino; and W is hydrogen, arylthio, alkylthio of 1 to 6 carbon atoms or methoxy, in combination with a pharmaceutically acceptable carrier.

12. A method of treating infections due to Bacillus, Staphylococcus and Streptococcus in animals including humans which comprises administering to such an animal in need thereof, a therapeutically effective amount of a compound of the formula (I):

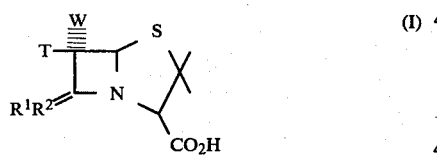

or a pharmaceutically acceptable salt thereof or a pharmaceutically acceptable ester thereof wherein $R^1$ and $R^2$ are each hydrogen, halo, a hydrocarbon of 1 to 10 carbon atoms unsubstituted or substituted by hydroxy, carboxy or alkoxycarbonyl of 1 to 6 carbon atoms in the alkoxy moiety, cyano or esterified carboxyl; T is hydrogen, amino or acylamino; and W is hydrogen, arylthio, alkylthio of 1 to 6 carbon atoms or methoxy, in combination with a pharmaceutically acceptable carrier.

13. A composition according to claim 11 wherein $R^1$ is hydrogen.

14. A composition according to claim 11 or 13 wherein $R^2$ is cyano, alkylcarbonyl of 1 to 6 carbon atoms in the alkyl moiety, alkoxycarbonyl of 1 to 6 carbon atoms in the alkoxy moiety, aryloxycarbonyl or aralkoxycarbonyl wherein the aryl moiety is phenyl or phenyl substituted by chloro, bromo, nitro or alkyl of 1 to 6 carbon atoms.

15. A composition according to claim 11 or 13 wherein $R^2$ is cyano, alkylcarbonyl of 1 to 6 carbon atoms or esterified carboxyl.

16. A composition according to claim 11 or 13 wherein $R^2$ is alkoxycarbonyl of 1 to 6 carbon atoms or benzyloxycarbonyl.

17. A composition according to claim 11 wherein T is amino or a group of the formula

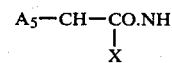

wherein $A_5$ is phenyl, hydroxyphenyl or thienyl and X is sulpho or carboxy or a salt or ester thereof.

18. A pharmaceutical composition useful for treating Bacillus, Staphylococcus and Striptococcus infections in animals including humans which comprises a therapeutically effective amount of a compound of the formula (II):

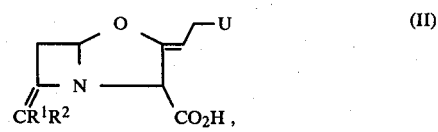

a pharmaceutically acceptable salt or pharmaceutically acceptable ester thereof, wherein $R^1$ and $R^2$ are each hydrogen, halo, a hydrocarbon of 1 to 10 carbon atoms unsubstituted or substituted by hydroxy, carboxy or alkoxycarbonyl of 1 to 6 carbon atoms in the alkoxy moiety, cyano or esterified carboxyl, and U is hydroxyl, substituted hydroxyl, thio, substituted thio, amino, mono- or di-hydroxycarbyl substituted amino, or mono- or di-acylamino, in combination with a pharmaceutically acceptable carrier.

19. A composition according to claim 18 wherein U is hydroxyl.

20. A method according to claim 12 wherein $R^1$ is hydrogen.

21. A method according to claim 12 or 20 wherein $R^2$ is cyano, alkylcarbonyl of 1 to 6 carbon atoms in the alkyl moiety, alkoxycarbonyl of 1 to 6 carbon atoms in the alkoxy moiety, aryloxycarbonyl or aralkoxycarbonyl wherein the aryl moiety is phenyl or phenyl substituted by chloro, bromo, nitro or alkyl of 1 to 6 carbon atoms.

22. A method according to claim 12 or 20 wherein $R^2$ is cyano, alkylcarbonyl of 1 to 6 carbon atoms or esterified carboxyl.

23. A method according to claim 12 or 20 wherein $R^2$ is alkoxycarbonyl of 1 to 6 carbon atoms or benzyloxycarbonyl.

24. A method according to claim 12 wherein T is amino or a group of the formula

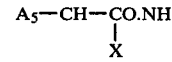

wherein $A_5$ is phenyl, hydroxyphenyl or thienyl and X is sulpho or carboxy or a salt or ester thereof.

25. A method of treating infections due to Bacillus, Staphylococcus and Streptococcus in animals, including humans which comprises administering to such an animal in need thereof a therapeutically effective amount of a compound of the formula (II):

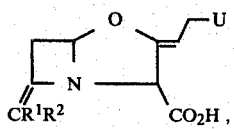 (II)

a pharmaceutically acceptable salt or pharmaceutically acceptable ester thereof, wherein $R^1$ and $R^2$ are each hydrogen, halo, a hydrocarbon of 1 to 10 carbon atoms unsubstituted or substituted by hydroxy, carboxy or alkoxycarbonyl of 1 to 6 carbon atoms in the alkoxy moiety, cyano or esterified carboxyl, and U is hydroxyl, substituted hydroxyl, thio, substituted thio, amino, mono- or di-hydroxycarbyl substituted amino, or mono- or di-acylamino, in combination with a pharmaceutically acceptable carrier.

26. A method according to claim 25 wherein U is hydroxyl.

* * * * *